United States Patent [19]
Grice et al.

[11] Patent Number: 5,437,682
[45] Date of Patent: Aug. 1, 1995

[54] MEDICAL KNOT TYING INSTRUMENT AND METHOD FOR USE THEREOF

[75] Inventors: O. Drew Grice, New Bern, N.C.; Thomas H. Benham, Clearwater; Michael Buhler, Madeira Beach, both of Fla.

[73] Assignee: Ideas for Medicine, Inc., Clearwater, Fla.

[21] Appl. No.: 94,771

[22] Filed: Jul. 20, 1993

[51] Int. Cl.$^6$ .................................................. A61B 17/00
[52] U.S. Cl. ............................. 606/148; 606/139; 606/205; 606/207
[58] Field of Search ............... 606/139, 148, 147, 151, 606/205-208

[56] References Cited

U.S. PATENT DOCUMENTS

| | | | |
|---|---|---|---|
| 532,306 | 1/1895 | Brown | 606/147 |
| 984,756 | 2/1911 | Frisch | 606/207 |
| 1,539,221 | 5/1925 | Tennant | 606/147 |
| 2,363,334 | 11/1944 | Jones | 606/147 |
| 2,455,833 | 12/1948 | Trombetta | 606/139 |
| 3,396,998 | 3/1967 | Scoville . | |
| 3,625,556 | 12/1971 | Stromberg . | |
| 3,828,791 | 8/1974 | Santos | 606/142 |
| 3,871,379 | 3/1975 | Clarke . | |
| 4,617,933 | 10/1986 | Hasson . | |
| 4,641,652 | 2/1987 | Hutterer et al. . | |
| 5,100,418 | 3/1992 | Yoon et al. . | |
| 5,129,912 | 7/1992 | Noda et al. . | |
| 5,133,724 | 7/1992 | Wilson, Jr. et al. | 606/207 |
| 5,152,769 | 10/1992 | Baber . | |
| 5,171,257 | 12/1993 | Ferzli | 606/205 |
| 5,234,443 | 8/1993 | Phan et al. | 606/205 |
| 5,250,054 | 10/1993 | Li | 606/139 |
| 5,261,917 | 11/1993 | Hasson et al. | 606/148 |
| 5,281,237 | 1/1994 | Gimpelson | 606/148 |
| 5,300,082 | 4/1994 | Sharpe et al. | 606/208 |

FOREIGN PATENT DOCUMENTS

| | | | |
|---|---|---|---|
| 46014 | 1/1911 | Germany | 606/207 |
| 1810806 | 6/1970 | Germany | 606/147 |
| 3808877 | 9/1989 | Germany | 606/205 |
| 3812165 | 10/1989 | Germany | 606/205 |

OTHER PUBLICATIONS

Ethicon, Endoscopic Knot Tying Manual, 1991, pp. 24-25.

*Primary Examiner*—Stephen C. Pellegrino
*Assistant Examiner*—Jeffrey A. Schmidt
*Attorney, Agent, or Firm*—William A. Birdwell

[57] ABSTRACT

A medical knot tying instrument having a first member including proximal and distal ends, a gripping mechanism for releasably gripping a first length of suture proximate the distal end of the first member and a holding mechanism for releasably holding a second length of suture proximate the location where the gripping mechanism grips the first length of suture but separated therefrom a predetermined distance toward the first member's proximal end. Gripping one length of suture using the gripping mechanism and holding a second length of suture using the holding mechanism, the instrument is rotated in one angular direction so that the second length of suture forms a loop around the instrument whereupon the second length is grasped using a separate grasping instrument. The second length is then released from the holding mechanism and the two lengths of suture are moved in opposite directions so that the loop slides along and off the instrument while the first length passes through the loop of the second length, thereby forming a throw of a knot.

46 Claims, 15 Drawing Sheets

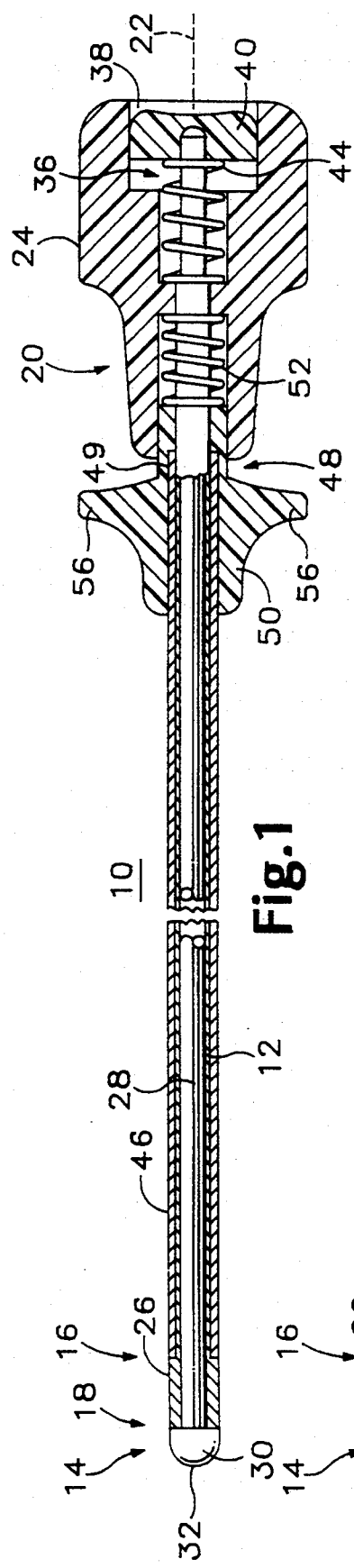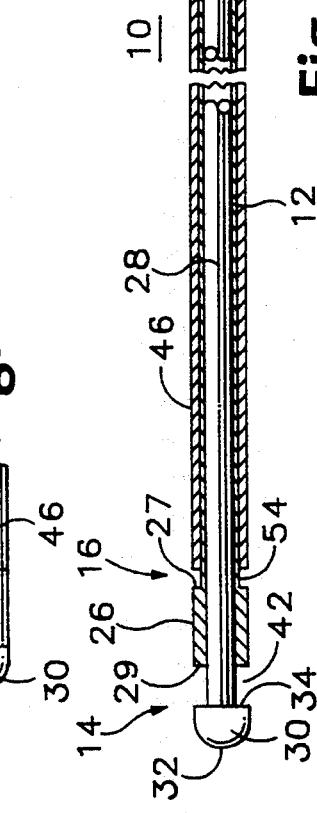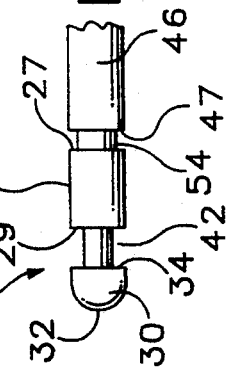

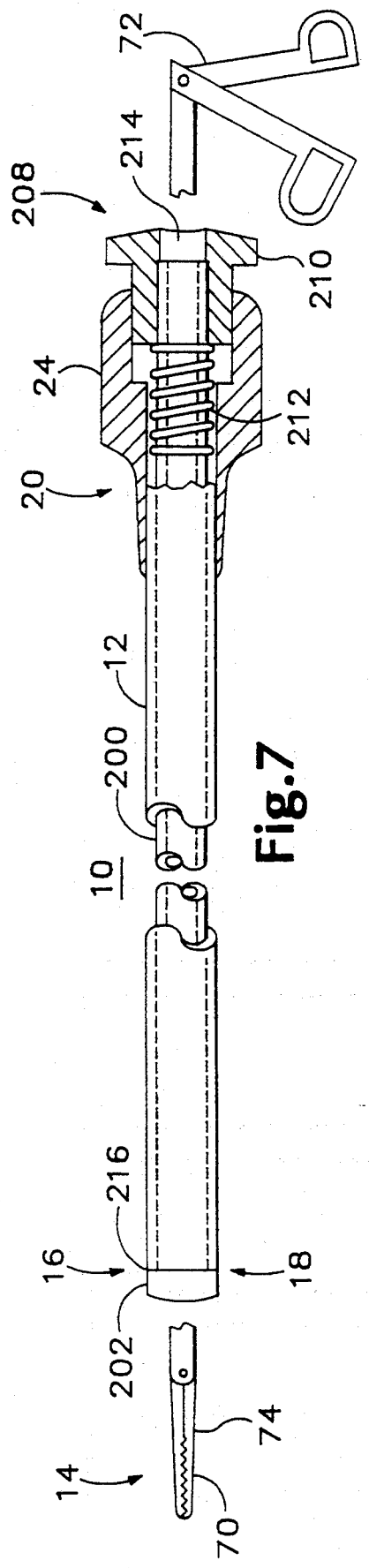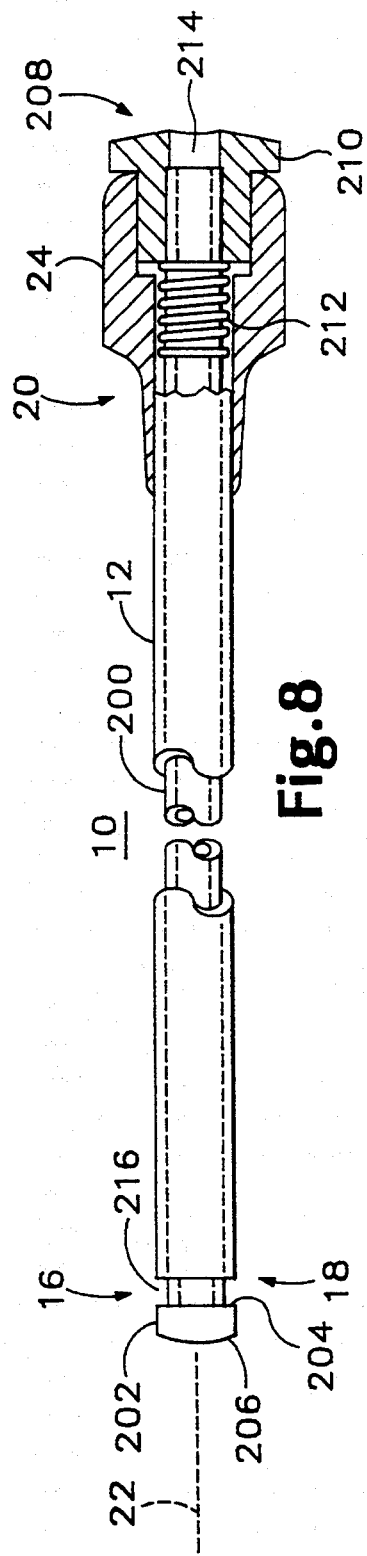

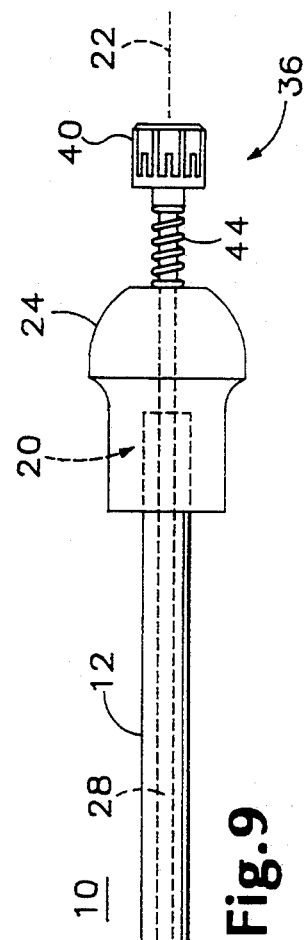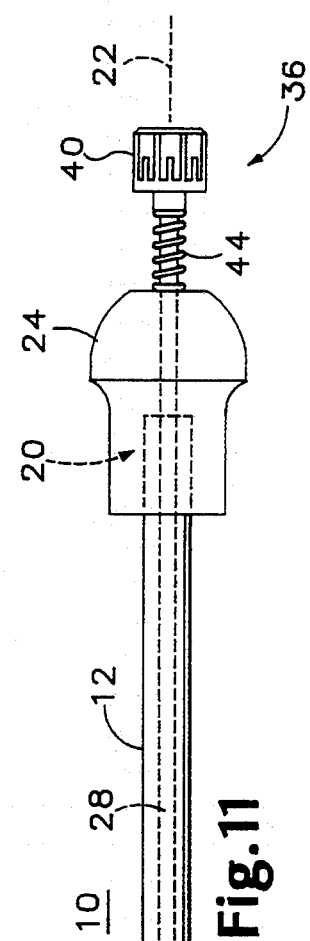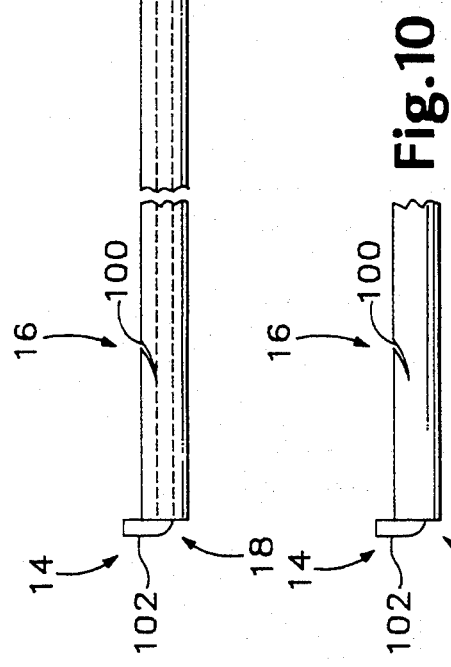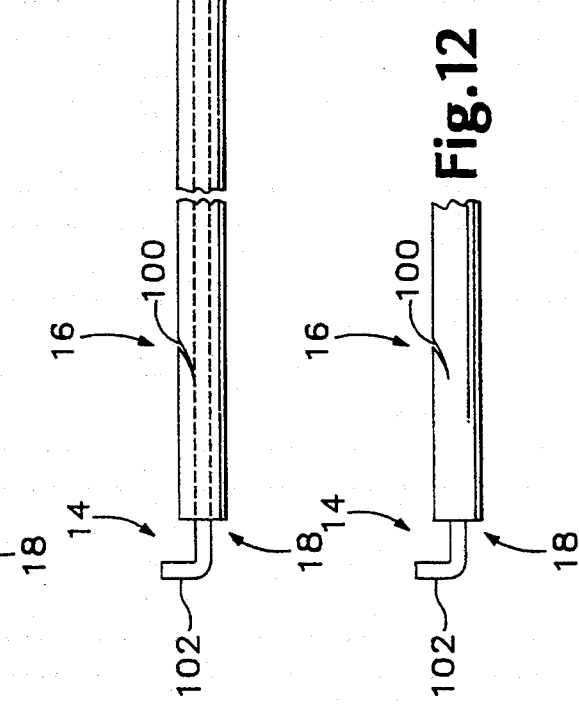

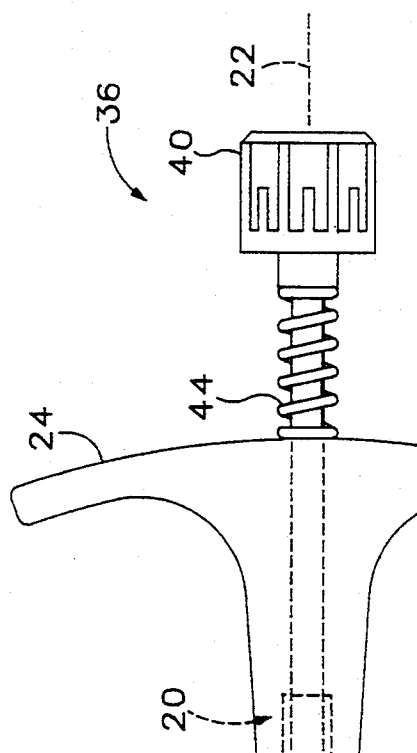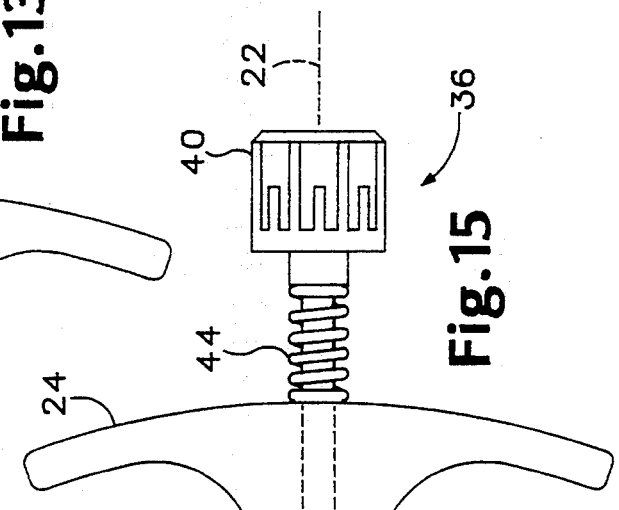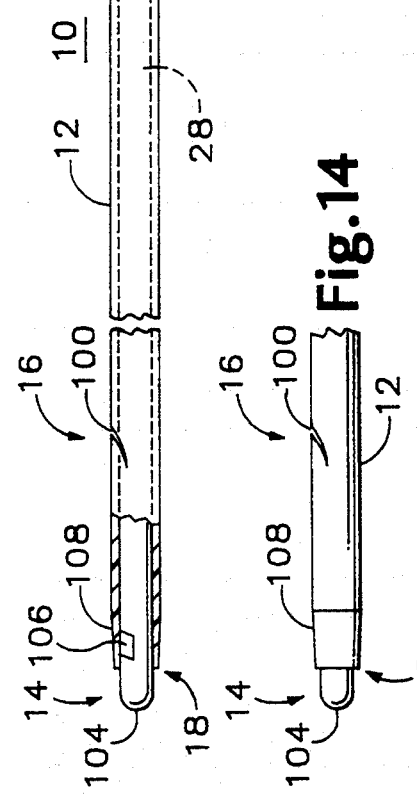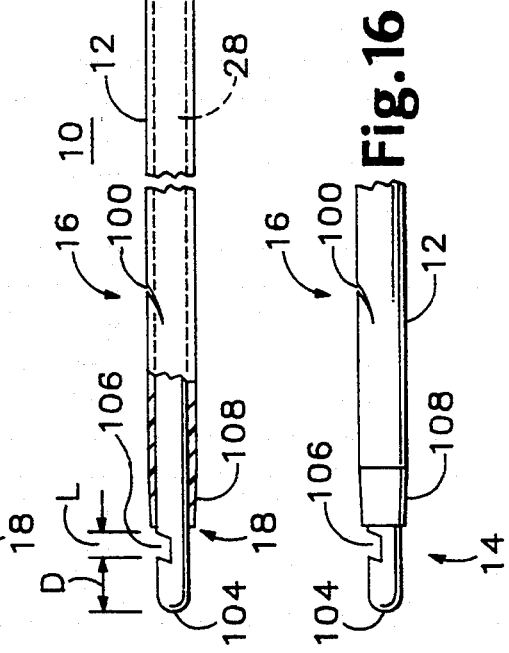

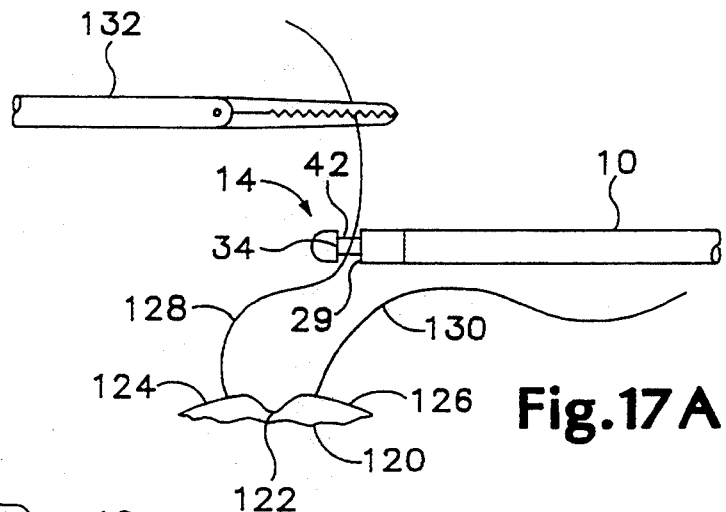
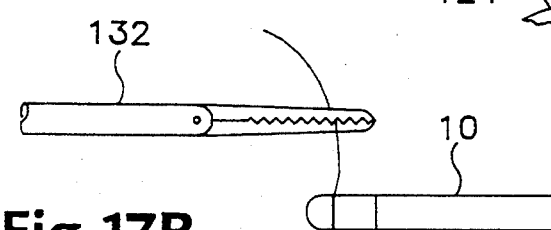
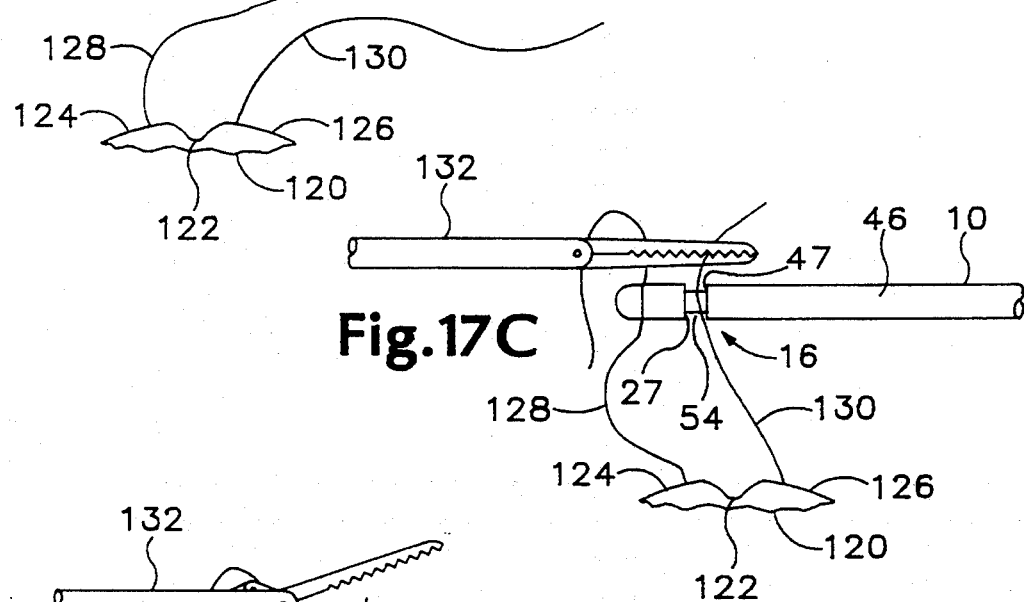
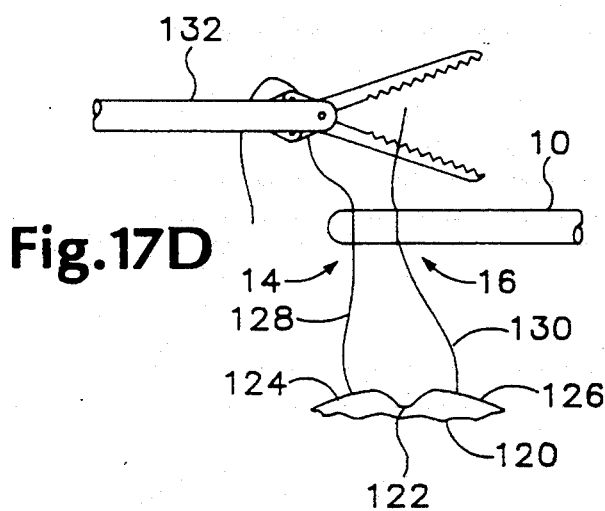

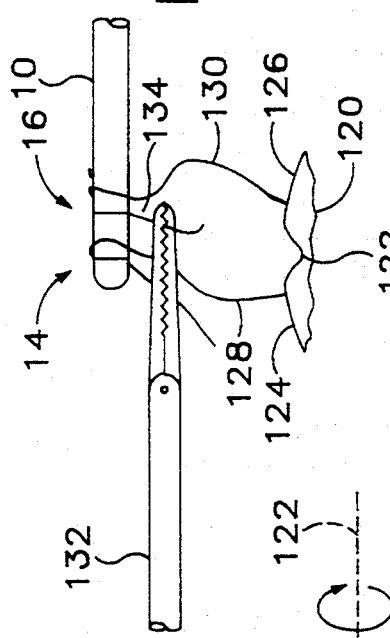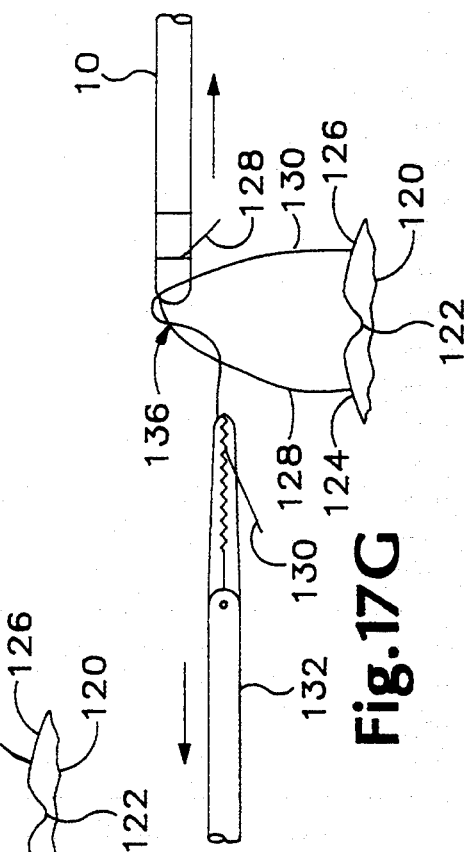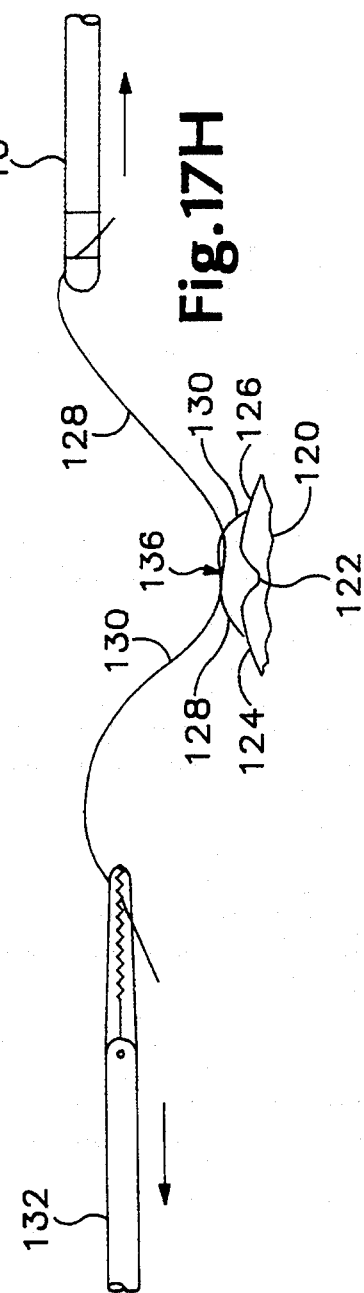

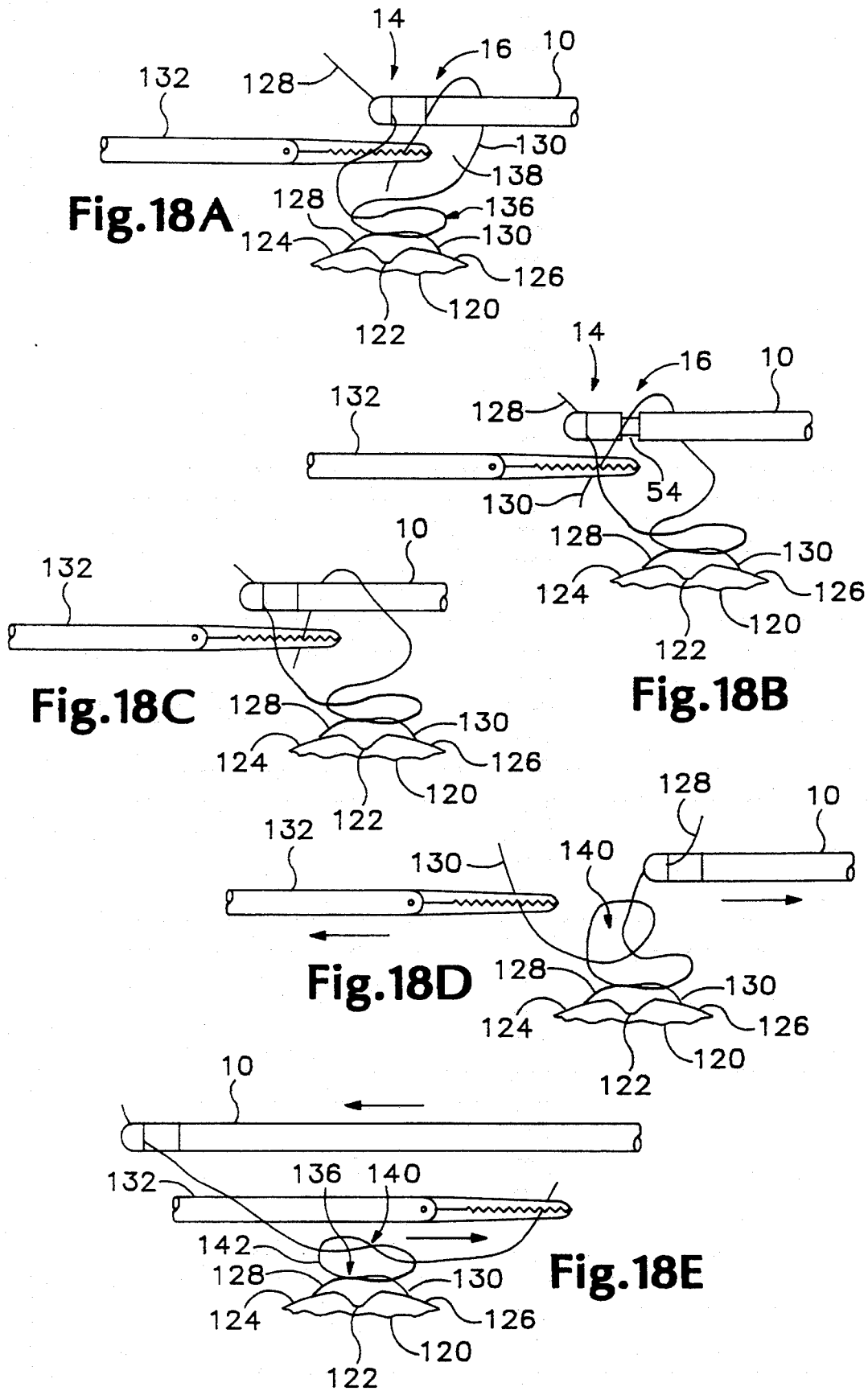

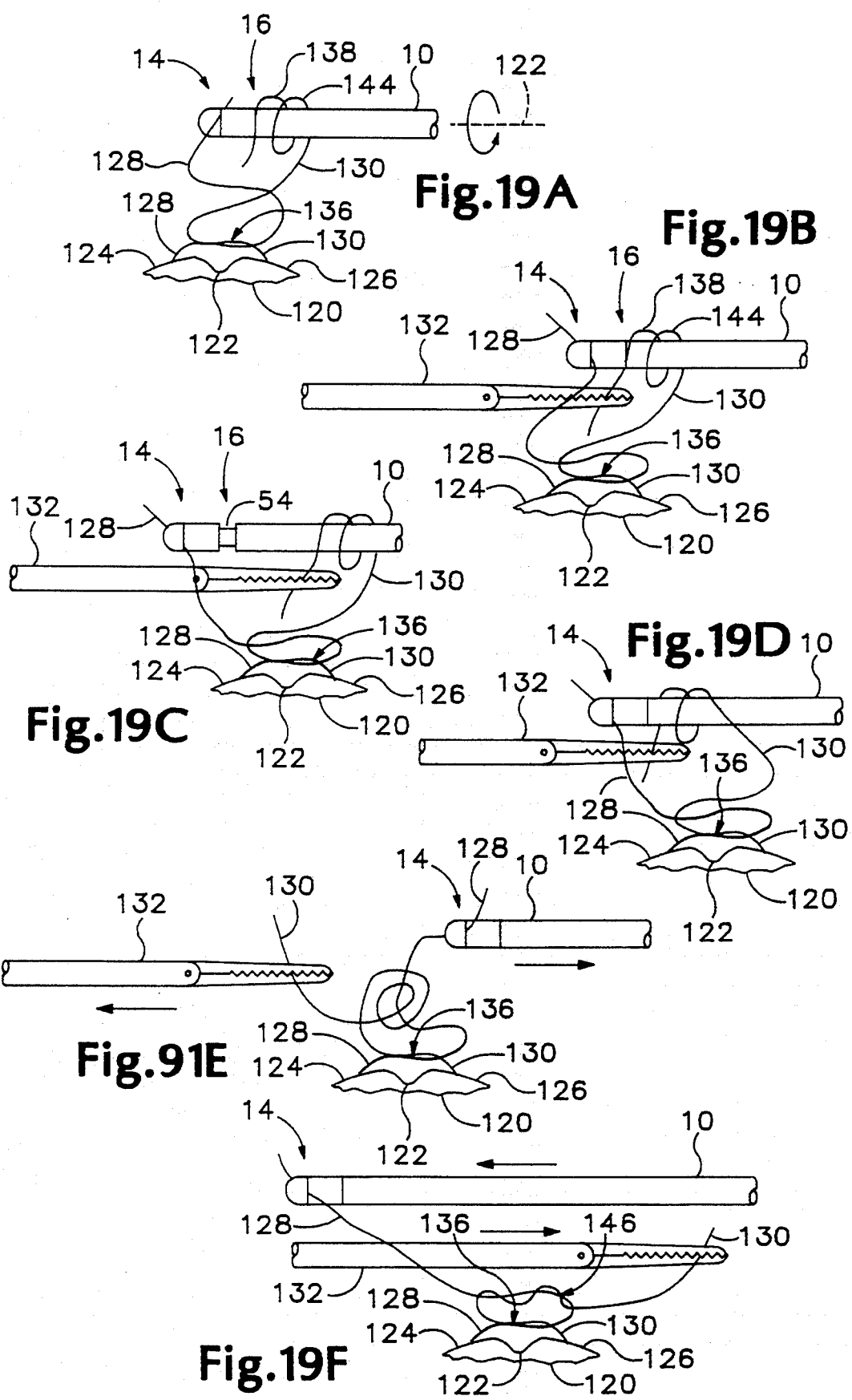

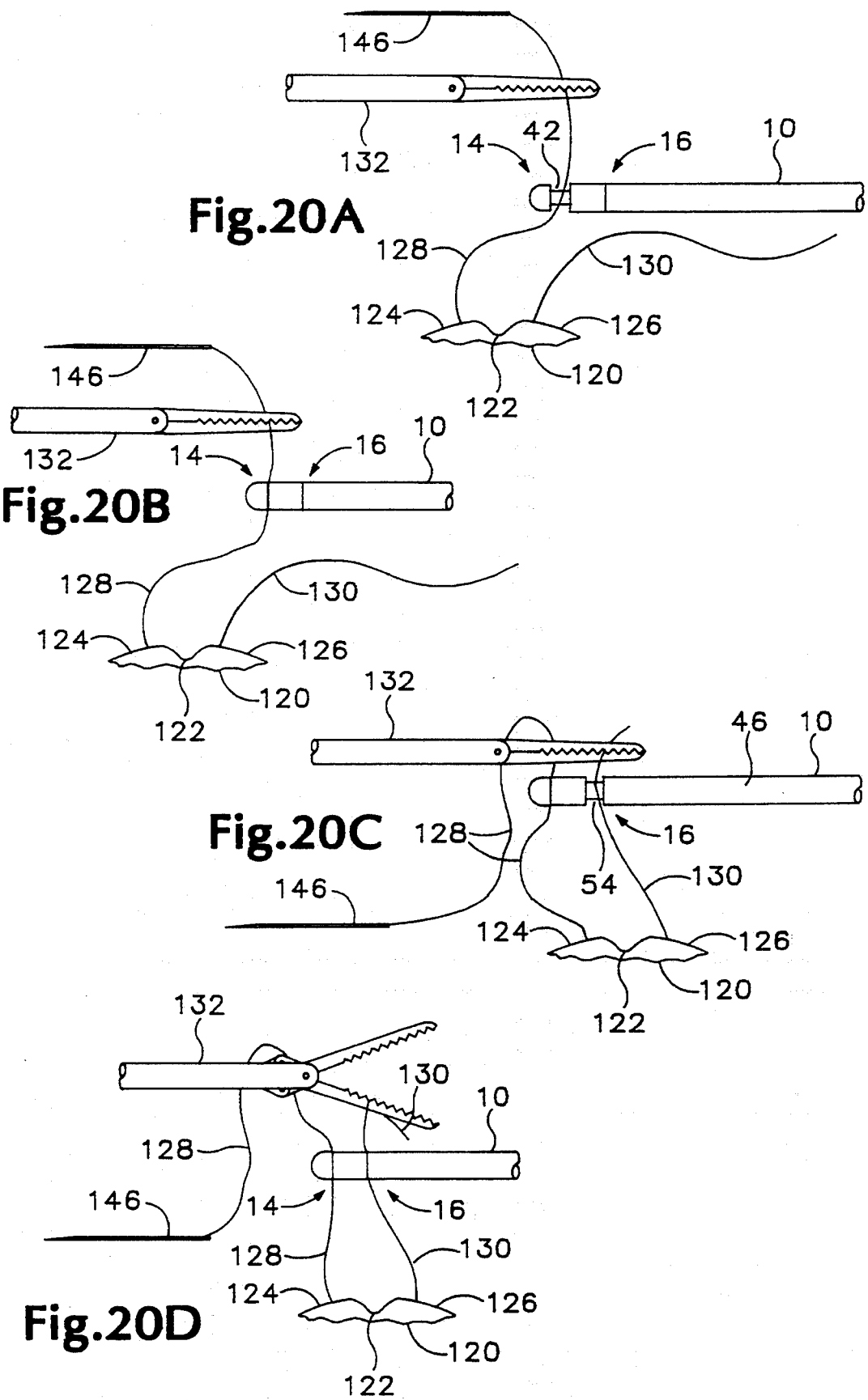

MEDICAL KNOT TYING INSTRUMENT AND METHOD FOR USE THEREOF

BACKGROUND OF THE INVENTION

This invention relates to medical instruments and methods for tying knots in a suture, particularly medical instruments and methods for tying knots in a suture at intracorporeal positions during least invasive surgery.

Least invasive surgery includes laparoscopic, endoscopic and orthoscopic surgeries. In performing laparoscopic surgery, for example, procedures are performed in the abdominal cavity by making a small incision through several layers of tissue, including the outer layer of skin called the epidermis, a layer of fat beneath the epidermis, a layer of abdominal muscle tissue beneath the fat layer and the lining of the abdominal cavity called the peritoneum. A trocar is inserted through the incision and medical instruments are introduced into the abdominal cavity therethrough. The surgeon performs procedures inside the cavity by manipulating the medical instruments from outside the patient while viewing the manipulations using a closed circuit monitor connected to an imaging device called a laparoscope that is inserted into the cavity. By using such equipment and procedures, laparoscopic surgery generally results in less trauma to the patient and, consequently, a more rapid recovery than with conventional open surgery. Similar advantages apply to other forms of least invasive surgery.

During least invasive surgery, it is necessary to close incisions made in intracorporeal tissue. Typically, each incision is closed by applying and tying a suture across the incision. In doing so it is generally desirable to use instruments that are easily manipulable and procedures that are efficient, so as to avoid unnecessary trauma to the patient.

Known instruments and procedures for tying sutures in least invasive surgery have a variety of forms, each having significant limitations. Noda et al. U.S. Pat. No. 5,129,912 ("Noda"), for example, discloses a knot tying device comprising a shaft that carries, at its distal end, a removable needle and a removable pre-formed knotted loop of suture. The needle is attached to one end of the knotted loop and the other end of the knotted loop extends to the proximal end of the shaft where it is attached to a tensioning device. In use, the instrument is introduced into the body cavity to a position proximate the incision to be closed, whereupon a second instrument is used to remove the needle, pass it through tissue on either side of the incision and then through the knotted loop, the knotted loop then being tightened using the tensioning device. Noda's instrument is undesirably limited in that it requires use of pre-formed knotted loops. Moreover, it requires manipulation of the needle to perform complex movements in tying knots. In addition, it is not designed to be used to tie two lengths of suture, as in a square knot.

Because conventional knot tying instruments and methods for their use have inherent limitations, a need exists for an improved instrument and method for tying knots in suture at intracorporeal positions during least invasive surgery.

SUMMARY OF THE INVENTION

The present invention fulfills the aforementioned need by providing a novel and improved medical instrument and method for tying knots in sutures, particularly for use in least invasive surgery. The instrument employs (i) an elongate, hollow first member having proximal and distal ends and a longitudinal axis, (ii) a gripping mechanism for releasably gripping a first length of suture proximate the distal end of the first member, and (iii) a holding mechanism for releasably holding a second length of suture proximate the location where the gripping mechanism grips the first length of suture but separated therefrom a predetermined distance toward the first member's proximal end.

In a preferred embodiment, the gripping mechanism comprises a second member slidably disposed within the first member and the holding mechanism comprises a third member slidably disposed over the first member, each member having proximal and distal ends. When the second and third members are slidably moved relative to the first member, gaps are openable and closable between the first member and the respective second and third members, proximate the distal ends thereof. The second and third members at their proximal ends have operating mechanisms to open or close the gaps and, thereby, receive or release a suture.

In a second embodiment, the gripping mechanism is provided by a conventional needle holder removably inserted through the first member. The second embodiment is otherwise substantially similar to the preferred embodiment.

In third and fourth embodiments, the holding mechanism is a V-shaped lateral notch formed in the first member into which a length of suture may be removably wedged, and the gripping mechanism is a second member, having distal and proximal ends, that is slidably disposed within the first member. The second member has, in the third embodiment, a hook at its distal end and, in the fourth embodiment, the second member has a lateral notch formed therein proximate its distal end. In both embodiments, the second member has an operating mechanism at its proximal end so as to move, respectively, the hook or the notch relative to the first member so that suture may be gripped thereby.

The knot tying instrument is used by gripping one length of suture using the gripping mechanism and holding a second length of suture using the holding mechanism. The instrument is then rotated in one angular direction about the first member's longitudinal axis so that the second length of suture forms a loop around the instrument whereupon the second length's end is grasped using a separate grasping instrument. The second length is then released from the holding mechanism and the two lengths of suture are moved in opposite directions so that the loop slides along and off the knot tying instrument while the first length passes through the loop, thereby forming a throw of a knot.

These steps are repeated a selected number of times to form additional throws in tying a knot. To tie a square knot, the steps are performed twice, a second throw being formed by rotating the lengths of suture in the direction opposite to that used in forming the first throw. To tie a surgeon's knot, the steps are as in tying a square knot, except the second throw is formed using two or more loops in the second length of suture. To tie a running knot wherein the end of the first length of suture is pre-attached to a needle, the first length of suture is gripped a predetermined distance from the needle so that, when each throw is formed, the first length of suture passes through the loop but the length's end and the needle attached thereto do not pass through the loop.

Accordingly, it is a principal object of the present invention to provide a novel and improved medical instrument and method for tying knots in sutures, particularly for use in least invasive surgery.

It is another object of the present invention to provide a knot tying instrument and method for its use that, when used in least invasive surgery, allow knots to be tied while minimizing trauma to surrounding tissue.

It is a further object of the present invention to provide a knot tying instrument and method for its use that minimizes the manipulations necessary to tie knots during least invasive surgery.

It is yet another object of the present invention to provide a knot tying instrument and method that are easy and efficient to use in tying knots in sutures.

It is yet a further object of the present invention to provide a knot tying instrument and method that facilitate the tying of various knots, including square knots.

It is another object of the present invention to provide a knot tying instrument that is lightweight.

It is a further object of the present invention to provide a knot tying instrument that is simple in design and easy and inexpensive to manufacture.

The foregoing and other objects, features and advantages of the invention will be more readily understood upon consideration of the following detailed description of the invention, taken in conjunction with the accompanying drawings.

BRIEF DESCRIPTION OF THE DRAWINGS

FIG. 1 is a side view of a preferred embodiment of a knot tying instrument according to the present invention, in partial section.

FIG. 2 is a side view of the distal end of the preferred embodiment of a knot tying instrument according to the present invention.

FIG. 3 is a side view of the preferred embodiment of a knot tying instrument according to the present invention, in partial section, with a member thereof forced to its forward position and another member thereof forced to its rearward position.

FIG. 4 is a side view of the distal end of the preferred embodiment of a knot tying instrument according to the present invention with a member thereof forced to its forward position and another member thereof forced to its rearward position.

FIG. 7 is a side view in partial section of a third embodiment of a knot tying instrument according to the present invention, using a needle holder and with a member thereof forced to its rearward position.

FIG. 8 is a side view in partial section of the third embodiment of a knot tying instrument according to the present invention, with a member thereof forced to its forward position.

FIG. 9 is a side view of a fourth embodiment of a knot tying instrument according to the present invention, in partial section.

FIG. 10 is a side view of the distal end of the fourth embodiment of a knot tying instrument according to the present invention.

FIG. 11 is a side view in partial section of the fourth embodiment of a knot tying instrument according to the present invention, with a member thereof forced to its forward position.

FIG. 12 is a side view of the distal end of the fourth embodiment of a knot tying instrument according the present invention, with a member thereof forced to its forward position.

FIG. 13 is a side view of a fifth embodiment of a knot tying instrument according to the present invention, in partial section.

FIG. 14 is a side view of the distal end of the fifth embodiment of a knot tying instrument according to the present invention.

FIG. 15 is a side view in partial section of the fifth embodiment of the knot tying instrument according to the present invention, with a member thereof forced to its forward position.

FIG. 16 is a side view of the distal end of the fifth embodiment of a knot tying instrument according to the present invention, with a member thereof forced to its forward position.

FIGS. 17A–17L show a side view of the preferred embodiment of a knot tying instrument according to the present invention, and illustrate the preferred method for use thereof to tie a knot in a suture according to the present invention.

FIGS. 18A–18E show a side view of the preferred embodiment of a knot tying instrument according to the present invention, and illustrate the preferred method for use thereof following the steps illustrated in FIGS. 17A–17L in tying a square knot.

FIGS. 19A–19F show a side view of the preferred embodiment of a knot tying instrument according to the present invention, and illustrate the preferred method for use thereof following the steps illustrated in FIGS. 17A–17L in tying a surgeon's knot.

DETAILED DESCRIPTION OF THE INVENTION

Figure 5:
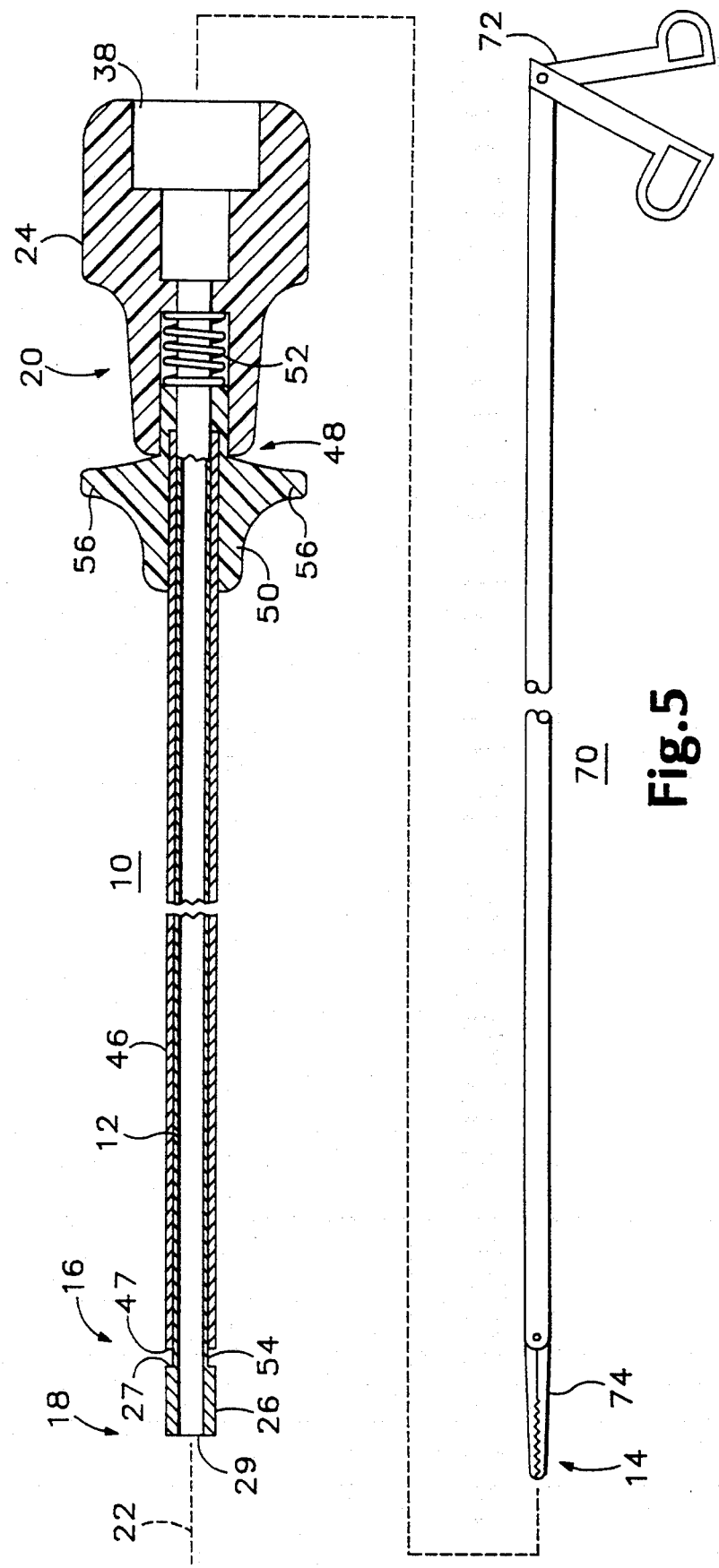
FIG. 5 is an exploded view in partial section of a second embodiment of a knot tying instrument according to the present invention, using a needle holder.

Referring to FIGS. 1–16, a medical knot tying instrument 10 according to the present invention generally comprises an elongate, hollow first member 12, a gripping mechanism 14 and a holding mechanism 16. The first member has a distal end 18, a proximal end 20, and a longitudinal axis 22. The first member 12, at its proximal end 20, is attached to a handle 24. The gripping mechanism 14 provides for releasably gripping a first length of suture proximate the distal end 18 of the first member 12. The holding mechanism 16 provides for releasably holding a second length of suture proximate the distal end 18 of the first member 12 at a predetermined distance toward the first member's proximal end 20 from where the first length of suture is gripped by the gripping mechanism 14. It is to be recognized that the distance between where the first length of suture is gripped by the gripping mechanism 14 and where the second length of suture is held by the holding mechanism 16 is determined according to a combination of factors, including the type of suture being used, the lengths of suture to be tied, the procedure with which the knot tying instrument is to be used, as well as other factors and, accordingly, may vary from instrument to instrument without departing from the principles of the invention.

Referring to FIGS. 1–4, a preferred embodiment of the knot tying instrument 10 according to the present invention is shown. The first member 12 has, at its distal end 18, an elongate collar 26 having a proximal face 27 and a distal face 29. The handle 24 is a figure of rotation centered on the longitudinal axis 22 of the first member 12 so as to provide facility in using the instrument 10, regardless of the rotational position thereof about the longitudinal axis 22. The gripping mechanism 14 comprises an elongate second member 28 slidably disposed within the first member 12, having a distal end and a proximal end.

Disposed at the distal end of the second member 28 is a head 30. The head 30 has a distal face 32 and proximal face 34, the distal face 32 being hemispherical so as to ease insertion of the instrument 10 through intracorporeal tissue. The second member 28 extends beyond the proximal end 20 of the first member 12, terminating in an operating mechanism 36. Preferably, the handle 24 provides a recess 38 within which the operating mechanism 36 is disposed, though it is to be recognized that the operating mechanism 36 may extend outside the handle 24 without departing from the principles of the invention.

The operating mechanism 36 comprises a push button 40 for selectively moving the second member 28 forward relative to the first member 12. So moving the second member 28 opens a first gap 42 between the head's proximal face 34 and the collar's distal face 29. The operating mechanism 36 further comprises a spring 44 which applies backward force on the second member 28. When the push button 40 is released, the spring 44 moves the second member 28 to a rearward position so as to bias the head's proximal face 34 against the collar's distal face 29, closing the first gap 42.

The holding mechanism comprises an elongate, hollow third member 46 having a distal end 47 and a proximal end 49. The third member 46 is slidably disposed over the first member 12 between the handle 24 and the collar's proximal face 27. The third member, at its proximal end 49, terminates in an operating mechanism 48. The operating mechanism 48 comprises a grip 50 for selectively moving the third member 46 rearward relative to the first member 12. So moving the third member 46 opens a second gap 54 between the collar's proximal face 27 and the third member's distal end 47. The operating mechanism 48 further comprises a spring 52 that applies forward force on the third member 46. When the grip 50 is released, the spring 52 moves the third member 46 to a forward position so as to bias the third member's distal end 47 against the collar's proximal face 27, closing the second gap 54.

Preferably, the grip 50 is provided with a pair of concave projections 56 extending laterally from opposite sides of the third member 46 so as to permit the user to place one finger in each of the respective concave projections 56 while cradling the handle 24 in the palm of the same hand or while operating the gripping mechanism 42 by selectively pushing and releasing the push button 40 using the thumb of the same hand.

The user pushes or releases the push button 40 selectively to open or close the first gap 42. When the first gap 42 is open, a suture may be received therein so that, when the first gap 42 substantially closes upon release of the push button 40, the suture is gripped between the head's proximal face 34 and the collar's distal face 29 due to the backward force applied by the spring 44. The user of the instrument 10 selectively pulls or releases the grip 50 to selectively open or close the second gap 54. When the second gap 54 is open, suture may be placed therein so that, when the second gap 54 substantially closes upon release of the grip 50, the suture is held between the third member's distal end 47 and the collar's proximal face 27 due to the forward force applied by the spring 52.

Preferably, the second member 28 has a round cross-section, and the first member 12 and third member 46 each have annular cross-sections. Similarly, the collar's proximal and distal faces 27 and 29 and the head's proximal face 34 preferably are annular, so that lengths of suture can be placed in the gaps 42 and 44 regardless of the rotational position of the instrument 10 about the longitudinal axis 22 of the first member 12. However, it is to be recognized that other cross-sectional shapes could be employed for the members and faces without departing from the principles of the invention.

It is also preferred that the head 30, the collar 26 and the distal end 47 of the third member 46 have uniform cross-sectional shapes where they meet so that, with the first gap 42 and the second gap 54 closed, the instrument 10 presents a smooth surface facilitating insertion of the instrument 10 into intracorporeal tissue. However, it is to be recognized that the head 30, the collar 26 and the third member's distal end 47 may have non-uniform cross-sectional shapes without departing from the principles of the invention. In any case, the maximum cross-sectional dimension of the instrument 10 should correspond to the internal diameter of the device, such as a trocar, through which the knot tying instrument 10 is introduced into the body cavity.

It is also to be understood that the length of the first and second gaps 42 and 54, respectively, are user-selectable by selectively pushing or releasing the push button 40 and pulling or releasing the grip 50. In this embodiment the maximum size of the first and second gaps 42 and 54 is substantially determined by the difference between the compressed and uncompressed lengths of the respective springs 44 and 52 of the operating mechanisms 36 and 48. In experimental trials, a maximum gap size of 1/16 inch has been used with satisfactory results.

Figure 6:
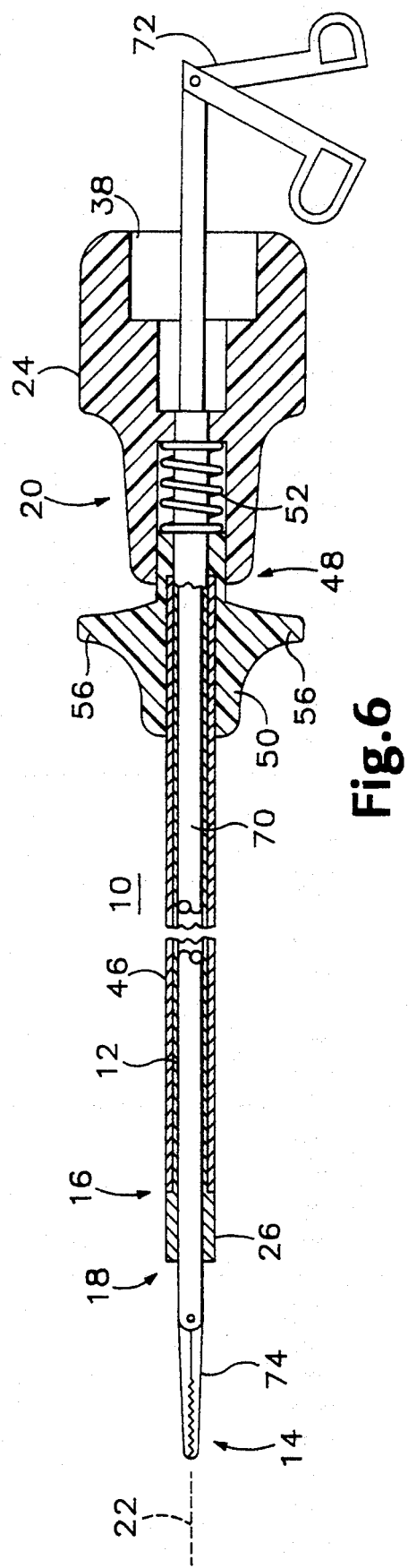
FIG. 6 is a side view of the second embodiment of a knot tying instrument according to the present invention, in partial section.

Referring to FIGS. 5 and 6, a second embodiment of the knot tying instrument 10 in accordance with the present invention is shown, wherein the gripping mechanism is provided by a conventional needle holder 70. Needle holders are well-known in the art having, as shown in the Figures, an operating mechanism 72 and a clamping mechanism 74. The needle holder 70 is removably inserted through the hollow first member 12 of the knot tying instrument such that the operating mechanism 72 extends from the handle 24 while the clamping mechanism 74 extends from the distal end 18 of the first member 12 so as to grip a suture. Although the needle holder 70 is used in place of the second member 28 of the preferred embodiment and its associated structure, it is to be recognized that the second embodiment is otherwise substantially the same as the preferred embodiment in structure and operation.

Referring to FIGS. 7 and 8, a third embodiment of the knot tying instrument 10 in accordance with the present invention is shown, wherein the gripping mechanism is provided by a conventional needle holder 70 having, as described above for the second embodiment, the operating mechanism 72 at the proximal end thereof and the clamping mechanism 74 at the distal end thereof. The holding mechanism 16 comprises an elongate, hollow member 200 slidably disposed within the first member 12, having a distal end and a proximal end.

Disposed at the distal end of the member 200 is a sleeve 202 having a proximal face 204 and a distal face 206. The distal face 206 is rounded so as to ease insertion of the instrument 10 through intracorporeal tissue. The member 200 extends beyond the proximal end 20 of the first member 12, terminating in an operating mechanism 208.

The operating mechanism 208 preferably comprises a push button 210 and a spring 212. The push button 210 includes a cylindrical aperture therethrough that is centered on the longitudinal axis 22 of the first member 10, through which the needle holder 70 is inserted. Pushing or releasing the push button 210 selectively opens or closes a gap 216 between the sleeve's proximal face 204 and the first member's distal end 18.

Generally, the operation of the operating mechanism 208 is substantially the same as the operation of the operating mechanism 36 and can be understood with reference to the description thereof.

Referring to FIGS. 9–16, fourth and fifth embodiments of the knot tying instrument 10 according to the present invention are shown. In both embodiments, the holding mechanism 16 comprises a V-shaped lateral notch 100 formed in the first member 12. The notch 100 is formed at a predetermined angle and is directed toward the distal end of the first member 12. The notch 100 has a predetermined depth and length so that a suture may be removably wedged therein. In both embodiments, the gripping mechanism 14 is substantially the same as the preferred embodiment, except with respect to the distal end of the second member 28.

In the fourth embodiment, the second member 28 has, at its distal end, a hook 102. The hook 102 extends a predetermined distance substantially perpendicularly to the longitudinal axis 22 of the first member 12. Although in FIGS. 9–12 the hook is shown to extend a distance beyond the first member 12, it is to be recognized that the hook 102 may be shorter or longer than the length shown without departing from the principles of the invention. The user pushes the push button 40 to move the hook 102 selectively away from the first member's distal end 18 so that a suture may be placed therebetween. When the push button 40 is released, the suture so placed is gripped between the hook 102 and the distal end 18 of the first member 12 by the backward force applied by the spring 44.

In the fifth embodiment, shown by FIGS. 13–16, the second member 28 has, at its distal end, a rounded tip 104 and has a lateral notch 106 spaced a distance D proximally from the tip 104. Preferably, the lateral notch 106 has a predetermined length L, as shown in FIG. 13. The distance D and the length L of the lateral notch 106 are chosen so that, when the push button 40 is fully depressed, the lateral notch 106 is entirely outside the first member 12 and, when the push button is released, the lateral notch 106 is biased by the spring 44 entirely within the first member 12. The tip 104 preferably is rounded so as to facilitate insertion of the instrument 10 into intracorporeal tissue. However, it is to be recognized that other shapes for the tip 104 may be used without departing from the principles of the invention. If the first member's distal end 18 is relatively thick, the distal end 18 preferably has a taper 108 so as to facilitate insertion of the instrument 10 into intracorporeal tissue.

In the fifth embodiment, the operating mechanism 36 operates in substantially the same way as it operates in the preferred and third embodiments, except that the lateral notch 106 is moved outside the first member 12 in order to receive a suture and, when the button 40 is released, the suture is drawn partially into the first member 12.

Preferably, in all embodiments the members 12, 28 and 46 are made of materials suitable for surgical use, such as stainless steel and nylon. It is also preferred that the materials provide sufficient rigidity and resiliency so that the instrument 10 may be flexed selectively during use, yet transmit adequate force from the respective proximal end to the distal end so as to be inserted through abdominal tissues, particularly abdominal muscle, and subsequently return to the original shape.

It is to be recognized that other materials, different shapes of handles 24 than those disclosed therein or in the Figures and different types of operating mechanisms 36 and 48 may be used without departing from the principles of the invention.

The method of use of the instrument 10 is illustrated in FIGS. 17A–17L through 20A–20Q. In those figures, intracorporeal abdominal tissue 120 is shown having an incision 122 to be closed. Extending from a first side 124 of the incision 122 is a first length 128 of suture. Extending from a second side 126 of the incision 122 is a second length 130 of suture. Although the figures, and descriptions thereof, illustrate the methods of use of the instrument 10 by reference to the preferred embodiment, it is to be recognized that the methods of use of the alternative embodiments are substantially similar and can be understood by reference to such figures and associated descriptions.

Referring first to FIGS. 17A–17L, the instrument 10 is used to tie the first length 128 and the second length 130 by gripping the first length 128 using the gripping mechanism 14 and holding the second length 130 using the holding mechanism 16, as shown in FIGS. 17A–17D. Using the preferred embodiment of the instrument 10, the first length 128 is gripped in the first gap 42 between the head's proximal face 34 and the collar's distal face 29, and the second length 130 is held in the second gap 54 between the collar's proximal face 27 and the distal end 47 of the third member 46. Although as shown in the figures, a grasping instrument 132 is used to place the lengths 128 and 130 in the respective gaps 42 and 54, it is to be recognized that the instrument 10 may be used without such grasping instrument 132, without departing from the principles of the invention. In particular, the instrument 10 may be used alone when the gaps 42 and 54 have annular cross-sections so as to receive a suture regardless of the rotational position of the instrument 10. It is also to be recognized that the respective operating mechanisms 36 and 48 are used to open and close the first and second gaps 42 and 54 to receive and retain a suture.

With the lengths 128 and 130 so gripped and held, the instrument 10 is then rotated in one angular direction about the longitudinal axis 22 of the first member 12 so that the second length 130 forms a first loop 134 around the instrument 10, as shown in FIG. 17E. The second length 130 is then grasped by the grasping instrument 132 between the end thereof and where it is held by the holding mechanism 16, as shown in FIG. 17F. The second length 130 of suture is then released from the holding mechanism 16, in this case, by pulling on the grip 50, and the first length 128, gripped by the gripping mechanism 14, and the second length 130, grasped by the grasping instrument 132, are then moved in opposite directions so that the first length 128 passes through the first loop 134 formed in the second length 130, thereby forming a first throw 136 of a knot, as shown in FIGS. 17G-17H. It is to be recognized that, in grasping the second length 130 using the grasping instrument 132, the grasping instrument 132 must be positioned relative to the first length 128 so that the first length 128 will pass through the first loop 134 to form the first throw 136 as shown in FIGS. 17F-17H.

Figure 17I:
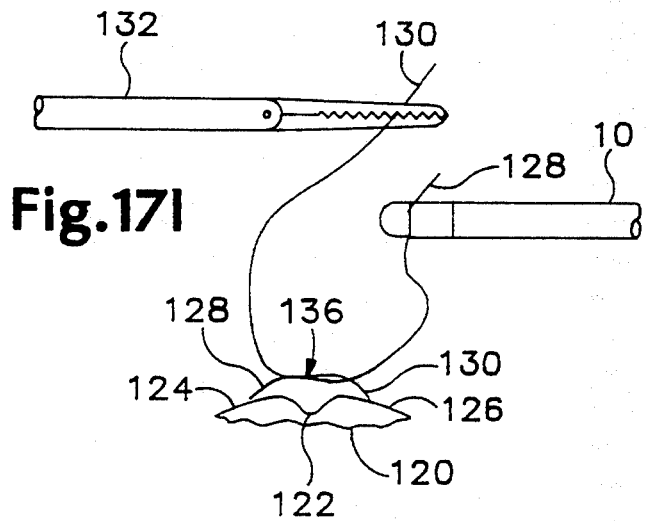
Figure 17J:
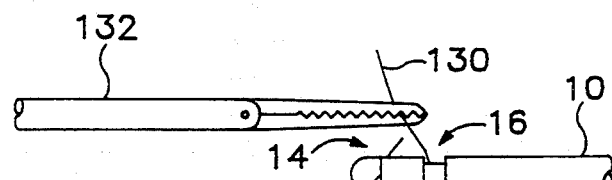
Figure 17K:
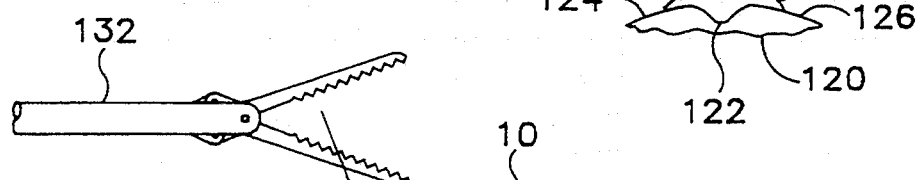
Figure 17L:
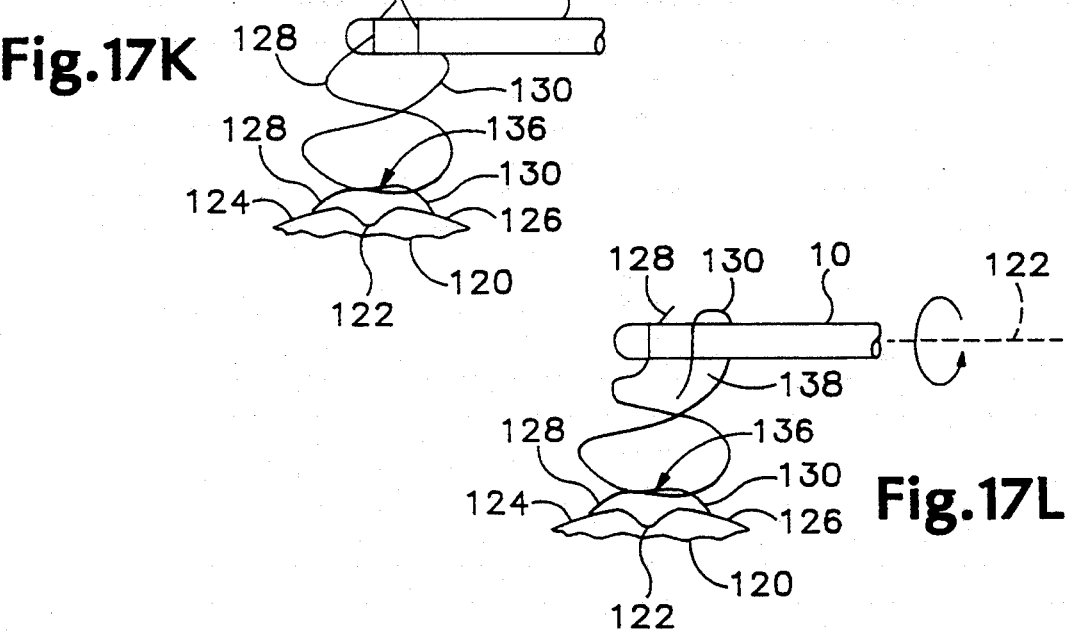

A knot is completed by gripping the first length 128 in the gripping mechanism 14 and holding the second length 130 in the holding mechanism 16, as described above and as shown in FIGS. 17I-17K. The instrument 10 is then rotated about the longitudinal axis 22 of the first member 12 in an angular direction opposite the angular direction used in forming the first throw 136, so as to form a second loop 138, as shown in FIG. 17L. At this point in the knot tying method, the user may selectively tie any of various knots, including a square knot or a surgeon's knot.

Referring to FIGS. 18A-18E, the remaining steps necessary to tie a square knot following the steps illustrated in FIGS. 17A-17L are shown. Having formed the second loop 138, the second length 130 is then grasped between the end thereof and the holding mechanism 16 using the grasping instrument 132, as shown in FIG. 18A. The second length 130 is then released from the holding mechanism 16, in this case by pulling on the grip 50 so as to open the second gap 54, as shown in FIG. 18B. The first length 128, gripped in the gripping mechanism 14, and the second length 130, grasped by the grasping instrument 132, are then pulled in opposite directions so that the first length 128 passes through the second loop 138 formed in the second length 130, so as to form a second throw 140, as shown in FIGS. 18C and 18D. It is to be recognized that, in grasping the first length 128 as shown in FIG. 18B, the grasping instrument 132 must be positioned relative to the first length 128 so that the first length 128 will pass through the second loop 138.

Following the formation of the second throw 140, the directions of movement of the grasping instrument 132 and the knot tying instrument 10 are reversed to cinch the second throw 140 onto the first throw 136, so as to tighten a square knot 142 so formed, as shown in FIG. 18E.

Referring to FIGS. 19A-19F, the remaining steps necessary to form a surgeon's knot following the steps illustrated in FIGS. 17A-17L are shown. Following formation of the second loop 138 as shown in FIG. 17L, the instrument 10 is further rotated about the longitudinal axis 22 of the first member 12 in the same angular direction shown in FIG. 17N, so as to form a third loop 144 in the second length 130, as shown in FIG. 19A. Following that step, a second throw 146 is formed by following steps illustrated in FIGS. 19B-19E which are substantially the same as, and will be understood from the description of, the steps described for FIGS. 18A-18D. In FIG. 19F, the directions of movement of the grasping instrument 132 and the knot tying instrument 10 are reversed from the directions of FIG. 19E to cinch the second throw 146 onto the first throw 136 so as to tighten a surgeon's knot 148.

Figure 20E:
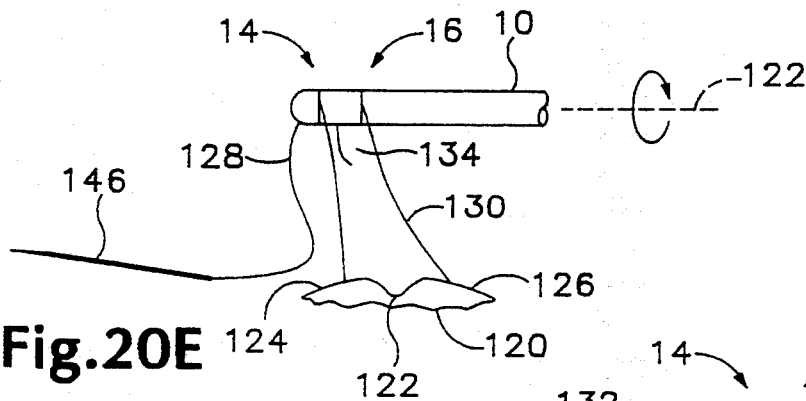
FIGS. 20A–20Q show a side view of the preferred embodiment of a knot tying instrument according to the present invention, and illustrate the preferred method for use thereof in tying a running suture knot.
Figure 20F:
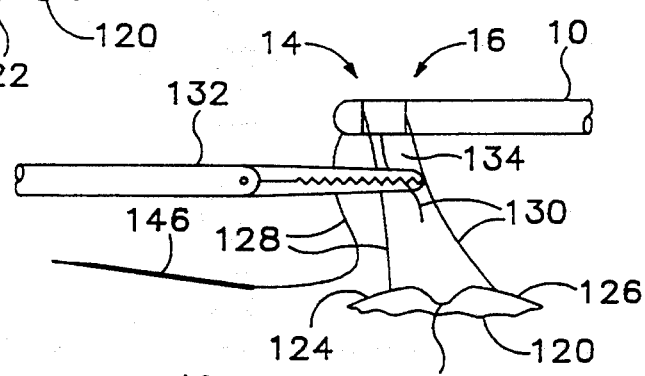
Figure 20G:
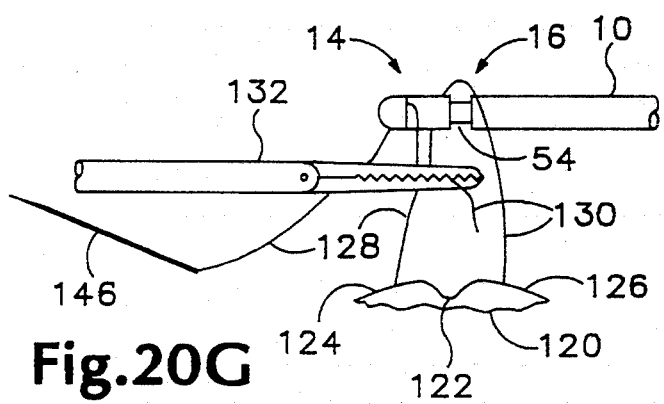
Figure 20H:
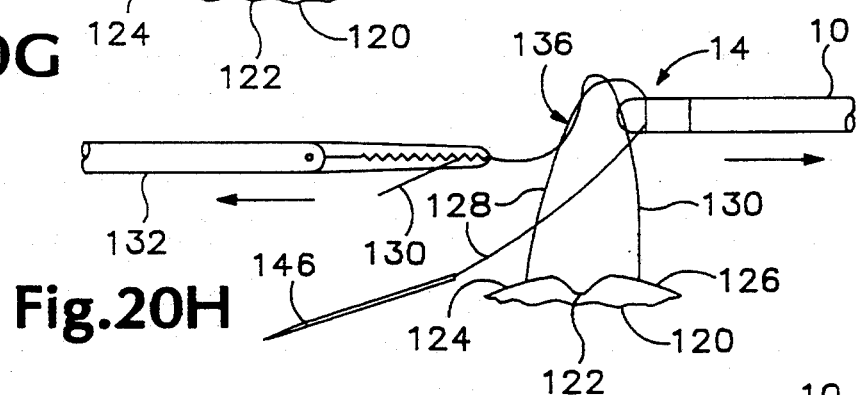
Figure 20I:
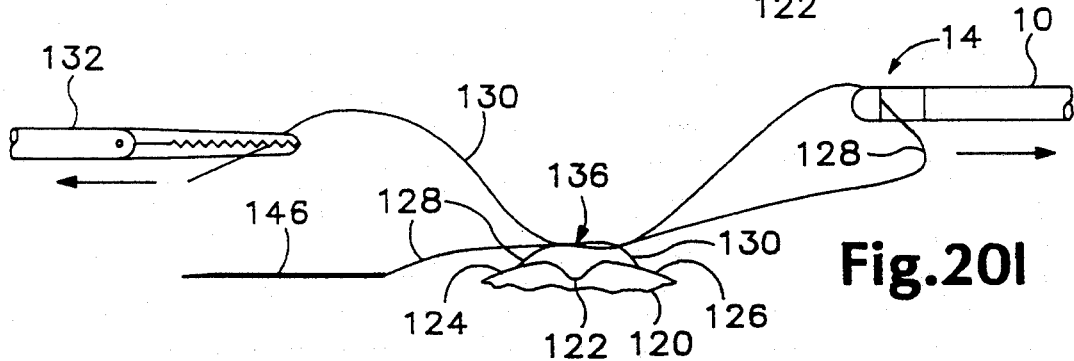
Figure 20J:
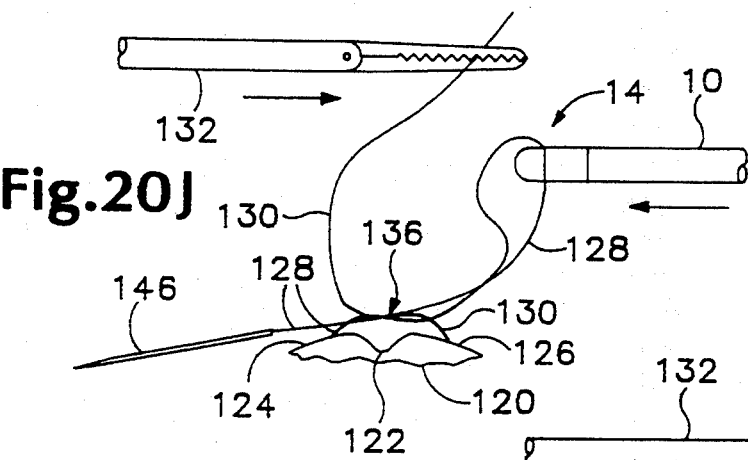
Figure 20K:
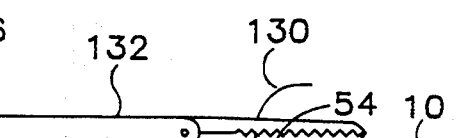
Figure 20L:
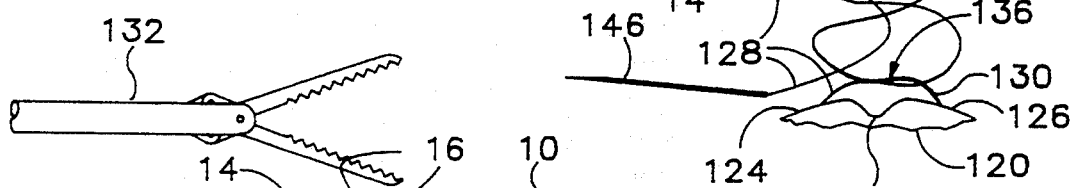
Figure 20M:
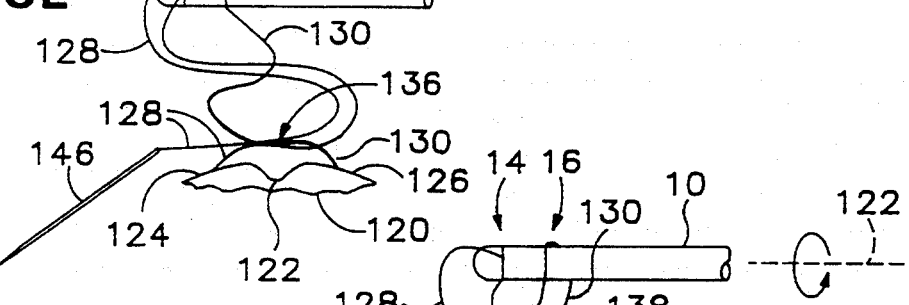
Figure 20N:
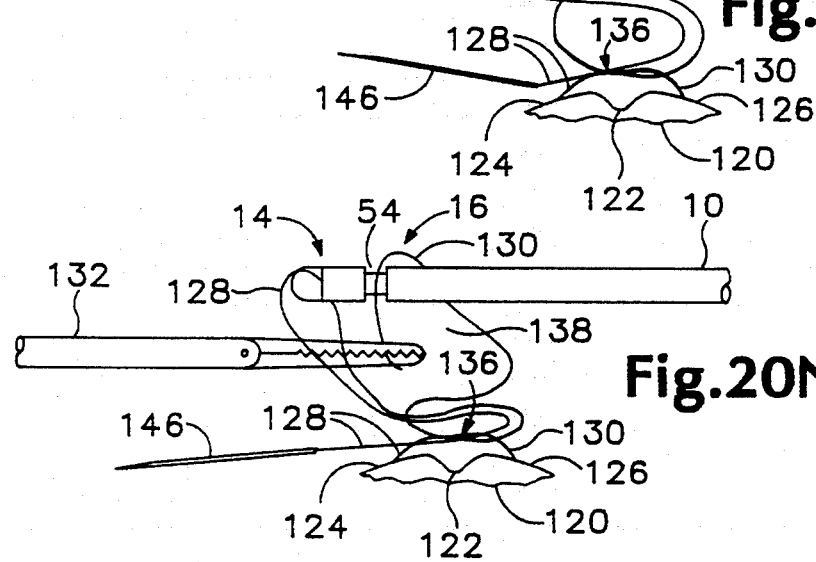
Figure 20O:
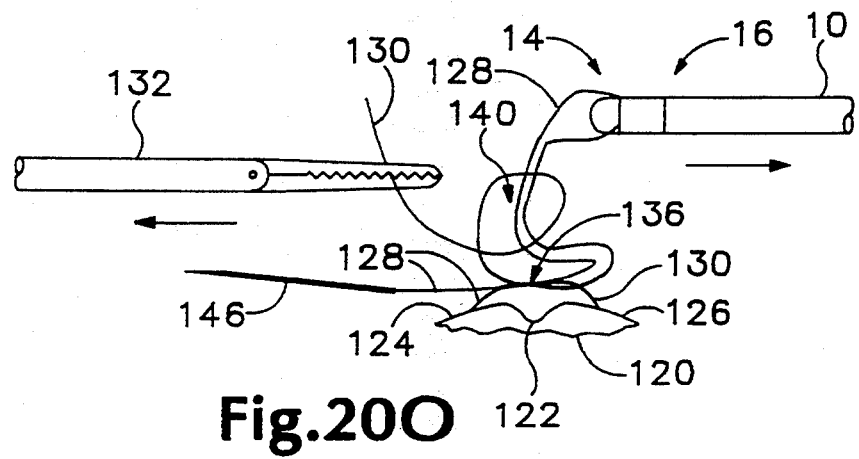
Figure 20P:
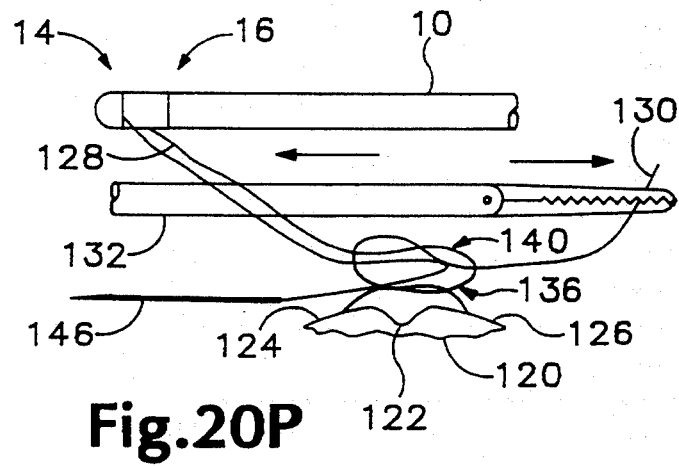
Figure 20Q:
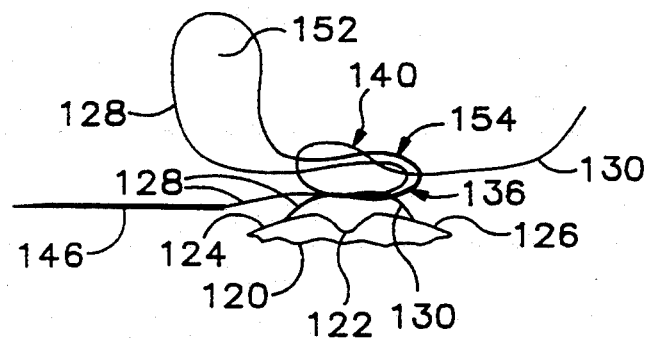

Referring to FIGS. 20A-20Q, the steps used in tying a running knot are shown. The steps are substantially the same as, and will be understood from the description of, the steps used to tie the square knot as illustrated in FIGS. 17A-17L and 18A-18E, except for variations to account for attachment of a needle 146 to the end of the first length 128. As shown in FIGS. 20A-20Q, the first length 128 is gripped by the gripping mechanism 14 at a predetermined distance from the needle 150 so that, in forming the throws of a surgeon's knot, the needle 150 will not pass through the loops formed in the second length 130 even though a portion of the first length 128 will pass through those loops. Specifically, FIG. 20B illustrates gripping the first length 128 at a distance from the needle 150. FIGS. 20H-20I and 20O-20P illustrate that the needle 150 does not pass through loops formed in the second length 130. As shown in FIG. 20Q, a loop 152 formed by the first length 128 extends from the resulting surgeon's knot 154.

The methods illustrated in FIGS. 17A-17L, 18A-18E, 19A-19F and 20A-20Q may be repeated any number of times to form additional throws in tying one or more knots, as selected by the user.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method for tying two lengths of suture using an elongate member having a proximal end, a distal end and a longitudinal axis, each length of suture having a respective end, comprising the steps of:
   (a) gripping a first length of suture by said elongate member proximate the distal end of said elongate member;
   (b) holding a second length of suture proximate the end of said suture by said elongate member at a position proximate, but separated from, the distal end of said elongate member;
   (c) rotating said elongate member about the longitudinal axis thereof in a first angular direction so as to form a first loop of said second length of suture around said elongate member;
   (d) grasping said second length of suture between the end of said second length of suture and said position where said second length of suture is held by said elongate member;
   (e) releasing said second length of suture from said elongate member; and
   (f) moving said first length of suture relative to said first loop so that said first length of suture passes through said first loop of said second length of suture so as to form a first throw.

2. The method of claim 1, further comprising, after step (f), pulling said first length of suture away from said second length of suture so as to tighten said first throw.

3. The method of claim 2, wherein the steps of claim are repeated so as to form a selected number of additional throws in tying a knot.

4. The method of claim 1, further comprising the additional steps of:
   (g) gripping said first length of suture by said elongate member proximate the distal end thereof;
   (h) holding said second length of suture proximate the end thereof by said elongate member at a position proximate, but separated from, the distal end of said elongate member;

(i) rotating said elongate member about the longitudinal axis thereof in a second angular direction being opposite to said first angular direction so as to form a second loop of said second length of suture around said elongate member;

(j) grasping said second length of suture between the end of said second length of suture and said position where said second length of suture is held by said elongate member;

(k) releasing said second length of suture from said elongate member; and (l) moving said first length of suture relative to said second loop so that said first length of suture passes through said second loop of said second length of suture so as to form a second throw.

5. The method of claim 4, wherein step (i) further comprises rotating said elongate member about the longitudinal axis thereof in said second angular direction through greater than 360 degrees so as to form two or more loops of said second length of suture around said elongate member.

6. The method of claim 4, wherein said first length of suture is gripped at a predetermined distance from the end thereof so that the end of said length of suture remains outside said first and second loops when moving said first length relative to said loops in respective steps (f) and (l) while the first length of suture where gripped at the distal end of said elongate member passes through said first and second loops in forming respective said first and second throws.

7. A medical instrument for tying two lengths of suture, comprising:
an elongate first member having a proximal end, a distal end and a longitudinal axis;
gripping means for releasably gripping a first length of suture proximate said distal end of said first member; and
holding means, disposed a predetermined distance proximally from said gripping means toward said proximal end of said first member, for releasably holding a second length of suture, said holding means and gripping means having a substantially common longitudinal axis.

8. The medical instrument of claim 7, wherein said first member is hollow.

9. The medical instrument of claim 7, wherein said gripping means comprises an elongate second member, having a proximal end and a distal end, slidably disposed within said first member, and a receiving means, disposed a predetermined distance proximally from said distal end of said second member, for securing the first length of suture.

10. The medical instrument of claim 9, wherein said second member and said receiving means comprise a needle holder.

11. The medical instrument of claim 9, wherein said receiving means comprises a lateral notch formed in said second member.

12. The medical instrument of claim 9, wherein said second member has a longitudinal axis, and said receiving means comprises a hook disposed at said distal end of said second member, said hook extending a predetermined distance substantially perpendicularly to said longitudinal axis of said second member.

13. The medical instrument of claim 9, wherein said second member has a head disposed at said distal end thereof and said receiving means comprises a gap formed between said head and said distal end of said first member, said gap being selectively openable and closable by sliding said second member relative to said first member.

14. The medical instrument of claim 13, wherein the gap formed between said head and said distal end of said first member is annular.

15. The medical instrument of claim 9, further comprising first operating means disposed at said proximal end of said second member for operating said gripping means.

16. The medical instrument of claim 15, wherein said first operating means comprises biasing means for applying proximally-directed force on said second member to bias said second member proximally relative to said first member.

17. The medical instrument of claim 16, wherein said biasing means comprises a spring.

18. The medical instrument of claim 16, wherein said first operating means further comprises actuating means for applying distally-directed force on said second member to overcome said proximally-directed force thereon.

19. The medical instrument of claim 18, wherein said actuating means comprises a push button attached to said proximal end of said second member.

20. The medical instrument of claim 15, wherein said holding means comprises a gap disposed a predetermined distance proximally from said receiving means, between said receiving means and said proximal end of said first member.

21. The medical instrument of claim 20, wherein said gap of said holding means comprises a V-shaped lateral notch formed in said first member, disposed at a predetermined angle toward said distal end of said first member.

22. The medical instrument of claim 20, further comprising a handle attached adjacent said proximal end of said first member, said first member having a longitudinal axis, and said handle extending laterally from said longitudinal axis of said first member.

23. The medical instrument of claim 20, wherein said holding means further comprises an elongate third member having a proximal end and a distal end, said third member being slidably disposed within said first member and having a sleeve disposed at said distal end thereof, said sleeve having a proximal face and a distal face, said proximal face of said sleeve of said third member and said distal end of said first member forming said gap therebetween, said gap being selectively openable and closable by sliding said third member relative to said first member.

24. The medical instrument of claim 7, wherein said holding means comprises a gap disposed a predetermined distance proximally from said distal end of said first member.

25. The medical instrument of claim 24, wherein said gap of said holding means comprises a V-shaped lateral notch formed in said first member, disposed at a predetermined angle toward said distal end of said first member.

26. The medical instrument of claim 1 wherein at least one of said gripping means nor holding means has opposed members which more relative to one another along said longitudinal axis of said first member.

27. A medical instrument for tying two lengths of suture comprising:
an elongate first member having a proximal end and a distal end, said distal end of said first member having a round cross-section of predetermined diameter;

gripping means for releasably gripping a first length of suture proximate said distal end of said first member, said gripping means comprising an elongate second member, having a proximal end and a distal end, slidably disposed within said first member, and a receiving means, disposed a predetermined distance proximally from said distal end of said second member, for securing the first length of suture, said second member having a head disposed at said distal end thereof, said head being shaped in a continuous curve and having a cross section substantially equal to said cross section of said distal end of said first member, and said receiving means comprising an annular gap formed between said head and said distal end of said first member, said gap being selectively openable and closable by sliding said second member relative to said first member; and holding means, disposed a predetermined distance proximally from said gripping means toward said proximal end of said first member for releasably holding a second length of suture.

28. A medical instrument for tying two lengths of suture, comprising:

an elongate first member having a proximal end and a distal end;

gripping means for releasably gripping a first length of suture proximate said distal end of said first member, said gripping means comprising an elongate second member, having a proximal end and a distal end, slidably disposed within said first member, and receiving means, disposed a predetermined distance proximally from said distal end of said second member, for securing the first length of suture;

holding means, disposed a predetermined distance proximally from said gripping means toward said proximal end of said first member, for releasably holding a second length of suture, said holding means comprising a gap disposed a predetermined distance proximally from said receiving means, between said receiving means and said proximal end of said first member, said holding means further comprising an elongate third member having a proximal end and a distal end, slidably disposed over said first member, said first member having a collar disposed proximate the distal end thereof, said collar having a proximal face and a distal face, said proximal face of said collar and said distal end of said third member forming said gap therebetween, said gap being selectively openable and closable by sliding said third member relative to said first member; and first operating means disposed at said proximal end of said second member for operating said gripping means.

29. The medical instrument of claim 28, further comprising second operating means disposed at said proximal end of said third member for opening and closing said gap of said holding means by controlling the position of said third member relative to said first member.

30. The medical instrument of claim 29, wherein said second operating means comprises biasing means for applying distally-directed force on said third member to bias said third member relative to said first member.

31. The medical instrument of claim 30, wherein said biasing means comprises a spring.

32. The medical instrument of claim 31, wherein said second operating means further comprises actuating means for applying proximally-directed force on said third member to overcome said distally-directed force thereon.

33. The medical instrument of claim 32, wherein said actuating means comprises a grip attached to said proximal end of said third member.

34. A medical instrument for tying two lengths of suture, comprising:

an elongate first member having a proximal end and a distal end;

gripping means for releasably gripping a first length of suture proximate said distal end of said first member; and holding means, disposed a predetermined distance proximally from said gripping means toward said proximal end of said first member, for releasably holding a second length of suture, said holding means comprising a gap disposed a predetermined distance proximally from said distal end of said first member; said holding means further comprising an elongate third member having a proximal end and a distal end, slidably disposed over said first member, said first member having a collar disposed proximate the distal end thereof, said collar having a proximal face and a distal face, said proximal face of said collar and said distal end of said third member forming said gap therebetween, said gap being selectively openable and closable by sliding said third member relative to said first member.

35. The medical instrument of claim 34, wherein said gap formed between said proximal face and said distal end is annular.

36. The medical instrument of claim 34, further comprising second operating means disposed at said proximal end of said third member for opening and closing said gap of said holding means by controlling the position of said third member relative to said first member.

37. The medical instrument of claim 36, wherein said second operating means comprises biasing means for applying distally-directed force on said third member to bias said third member relative to said first member.

38. The medical instrument of claim 37, wherein said biasing means comprises a spring.

39. The medical instrument of claim 38, wherein said second operating means further comprises actuating means for applying proximally-directed force on said third member to overcome said distally-directed force thereon.

40. The medical instrument of claim 39, wherein said actuating means comprises a grip attached to said proximal end of said third member.

41. A medical instrument for tying two lengths of suture, comprising:

an elongate first member having a proximal end, a distal end and a longitudinal axis;

gripping means for releasably gripping a first length of suture proximate said distal end of said first member; and holding means, disposed a predetermined distance proximally from said gripping means toward said proximal end of said first member, for releasably holding a second length of suture, at least one of said gripping means or holding means being adapted to receive a suture at any point around the circumference of said instrument, said holding means and gripping means having a substantially common longitudinal axis.

42. A medical instrument for tying two lengths of suture, comprising:
an elongate first member having a proximal end, a distal end, and a cross section;
gripping means for providng a closeable first gap for releasably gripping a first length of suture proximate said distal end of said first member;
holding means, disposed a predetermined distance proximally from said gripping means toward said proximal end of said first member, for providing a closeable second gap for releasably holding a second length of suture; and
a collar disposed between said gripping means and holdng means, said collar having a proximal face and a distal face, said proximal face comprising a proximal side of said first gap and said proximal face comprising a distal side of said second gap.

43. The medical instrument of claim 42, wherein said holding means is capable a length of suture at a plurality of points around said cross section.

44. The medical instrument of claim 43, wherein said plurality of points amount to at least 180° around said cross section.

45. A medical instrument for tying two lengths of suture, comprising:
an elongate first member having a proximal end, a distal end, a longitudinal axis, and a cross section;
gripping means for releasably gripping a first length of suture proximate said distal end of said first member; and
holding means, disposed a predetermined distance proximally from said gripping means toward said proximal end of said first member, for releasably holding a second length of suture, said suture being receivable by said holding means at a plurality of points which amount to at least 185° around said cross section wherein said holding means has opposed members which move relative to one another along said longitudinal axis so as to grip the suture therebetween.

46. The medical instrument of claim 45, wherein said points amount to at least 270° around said cross section.

* * * * *